United States Patent [19]

Orren

[11] 3,934,004

[45] Jan. 20, 1976

[54] STAIN RESISTANT ANTI-PERSPIRANT COMPOSITION

[76] Inventor: Leonard J. Orren, 8408 Wornall Road, Kansas City, Mo. 64111

[22] Filed: Mar. 9, 1973

[21] Appl. No.: 339,934

[52] U.S. Cl. .................................. 424/68; 424/47
[51] Int. Cl.² .......................................... A61K 7/38
[58] Field of Search .......... 424/175, 164, 68, 66, 65

[56] References Cited
UNITED STATES PATENTS

| | | | |
|---|---|---|---|
| 2,230,082 | 1/1941 | Montenier | 424/68 |
| 2,236,387 | 3/1941 | Wallace, Jr. et al. | 424/68 |
| 3,429,967 | 2/1969 | De Luca et al. | 424/175 |

*Primary Examiner*—Dale R. Ore
*Attorney, Agent, or Firm*—Berman, Aisenberg & Platt

[57] ABSTRACT

Staining in the underarm areas of garments due to the presence of perspiration and the residue of an aluminum salt containing anti-perspirant is preventable by incorporating into the anti-perspirant composition specific water soluble mild reducing agents including various sulfur or phosphorus compounds or stannous or titanous salts. Alternatively, the reducing agents rather than being incorporated into the anti-perspirant composition may be employed to treat the soiled garments prior to washing or dry cleaning the garments.

5 Claims, No Drawings

STAIN RESISTANT ANTI-PERSPIRANT COMPOSITION

BACKGROUND OF THE INVENTION

The present invention relates to anti-perspirant compositions for topical application, and more particularly to aluminum salt containing anti-perspirant compositions containing selected reducing agents to prevent the formation of stains in soiled garments.

Anti-perspirant compositions containing metallic salts with astrigent action is well known. Aluminum salts such as aluminum chloride and aluminum chlorhydrate have found wide commercial acceptance in such compositions which are usually applied to reduce sweating in the axillary regions.

One commonly encountered but unpublicized limitation inherent in the use of aluminum salt containing anti-perspirant compositions such as roll-on lotions, creams and aerosols is their capacity in varying degrees to cause staining of garments in regions where both perspiration and the anti-perspirant have been absorbed from the surface of the skin of the wearer into the fabric of the garment. This results in the development of the familiar underarm staining of garments. This unsightly staining, particularly of outer garments, may preclude further wearing of such garments and necessitate premature replacement of these garments.

The stains in question are characterized by the appearance of a yellow discoloration in the regions of the garments which have been exposed to the combined effect of perspiration and the anti-perspirant composition. This stain does not develop immediately after the wearing of the garment. In general the discoloration appears only after an extended period of time during which the garment has been repeatedly worn and dry-cleaned or laundered.

SUMMARY OF THE INVENTION

It is a primary object of the present invention to prevent or at least substantially reduce the staining heretofore found to occur in regions of garments exposed to a combination of perspiration and an aluminum salt containing anti-perspirant composition. Another primary object of the present invention is to provide a method for treating soiled garments containing perspiration and residual material from an aluminum salt containing anti-perspirant composition of conventional formulation with selected water-soluble reducing agents prior to laundering or dry cleaning the garments to prevent the development of stains in the garments.

The stain resulting from the use of aluminum salt anti-perspirant compositions apparently does not become immediately apparent due to the relative efficiency of the aluminum compounds in inhibiting perspiration. In general the extent of such inhibition is thought to be between 40% and 90% compared to an untreated control, depending upon such variables as the particular anti-perspirant formulation, the wearer, and climatic conditions. Thus, after the initial wearing of a garment by a person who has employed an aluminum salt containing anti-perspirant, the total quantity of perspiration deposited in the fabric of the garment may be quite small. It may require repeated use of the garment before a sufficient build-up of a perspiration - anti-perspirant interaction product occurs to manifest itself in the formation of a yellow stain in the fabric of the garment.

It has now been discovered that the observed staining of fabrics which have been exposed to the combined interaction of perspiration and aluminum salt containing anti-perspirant results from the reaction of the eccrine component of sweat with the aluminum salt containing anti-perspirant. Heretofore the excretions from the eccrine sweat glands have been thought to be of lesser importance with regard to perspiration problems and the maintenance of personal hygiene than the excretions from the apocrine sweat glands. Apocrine sweat is a whitish, odorless liquid which contains considerable amounts of lipid materials as compared to eccrine sweat which is essentially water containing very small amounts of sodium chloride. Although apocrine sweat is itself odorless, bacteria on the surface of the skin can act upon the lipid content of the sweat to form odorous compounds.

The significance of eccrine excretion in stain formation was determined experimentally. Perspiration derived from the back and chest in the course of vigorous physical exercise was leached from a number of saturated undershirts and concentrated by evaporation. The concentrates were extracted with ethyl ether to remove any lipid apocrine contamination. The resulting concentrate was applied to fresh, clean undershirts, and repeatedly treated with aluminum salt anti-perspirant. After drying the shirts were exposed to the combined action of moisture and heat to reproduce the conditions normally encountered in washing and drying cycles. On examination the garments were found to develop bright yellow stains in the areas exposed to perspiration and anti-perspirant. In other experiments synthetically prepared eccrine perspiration was applied to clean undershirts in a similar fashion and was also found to cause yellow staining.

The objectives of the present invention may be achieved either by incorporating into the anti-perspirant composition or by applying to the effected areas of the garments immediately prior to washing of the garments specified reducing agents which act to prevent the development of an anti-perspirant yellow stain during subsequent cleaning of the garments.

The useful reducing agents include both organic and inorganic reducing agents which are water soluble or water dispersible and are cosmetically acceptable, i.e., they are non-staining, non-irritating to skin, and essentially odorless. For the purposes of this application, the term "water dispersible" will hereinafter be employed to include reducing agents which, in water, form either a dispersion or a solution. The foregoing criteria exclude from use in the present invention such known reducing agents as inorganic sulfides, certain thiols, such as thioglycolic acid and thioglycerol, nitrites, arsenites, formates, oxalates, ferrous salts, hydrazines, hydroxylamines, acetaldehyde, glucose, reducing sugars, sugar amines, ascorbic acid, hydroquinone, and sodium borohydride.

Although it is not intended to be bound by the veracity of any theory, it is believed that the selected reducing agents of the invention prevent the development of stain by hindering the reaction of eccrine perspiration with the aluminum compound from forming yellow-colored reaction materials under the influence of heat and moisture. It is believed that the reducing agents cause the interaction product of perspiration and the aluminum compound to be retained in a colorless, soluble condition so that it can readily be washed from the garments leaving no residual stain.

DETAILED DESCRIPTION OF THE INVENTION

A wide variety of diverse reducing agents may be employed in carrying out the invention. It is essential that these reducing agents be cosmetically acceptable so as not to cause skin irritations or to add objectionable odors, and reducing agents must be water dispersible. Suitable reducing agents having these properties include a number of organic and inorganic sulfur-or phosphorus-containing compounds as well as a number of stannous or titanous salts which may be either organic or inorganic salts.

Useful inorganic sulfur-containing reducing agents include the following:

a. Sulfites, such as ammonium, alkali-metal, alkaline-earth-metal and zinc sulfites, including $(NH_4)_2SO_3$, $Na_2SO_3$, $CaSO_3$, $ZnSO_3 \cdot 2H_2O$, $Li_2SO_3$ and $K_2SO_3$;

b. Bisulfites, such as ammonium, alkali-metal and alkaline-earth-metal bisulfites, including $(NH_4)HSO_3$, $NaHSO_3$, and $Ca(HSO_3)_2$;

c. Hydrosulfites (dithionites), such as sodium dithionate, $Na_2S_2O_4$ and zinc dithionate, $ZnS_2O_4$;

d. Metabisulfites (pyrosulfites), such as alkali metal metabisulfites, including $Na_2S_2O_5$ and $K_2S_2O_5$; and, e. Thiosulfates, such as alkali-metal and alkaline-earth-metal thiosulfates, including $Na_2S_2O_3$ and $CaS_2O_3$.

Useful organic sulfur-containing reducing agents include organic salts, such as organic bisulfites, in which the bisulfite group has replaced the hydrogen atom of an amino group, including monoethanolamine bisulfite, urea bisulfite, guanidine bisulfite, ethylamine bisulfites, and ethylenediamine bisulfite as well as higher linear and branched chain homologs and polymers thereof; and adducts of sulfur dioxide which are addition products formed between low molecular weight aldehydes or ketones and sodium or zinc bisulfite, such as sodium formaldehyde bisulfite, sodium formaldehyde sulfoxylate, zinc formaldehyde sulfoxylate, and acetone sodium bisulfite.

The use of cosmetically acceptable thiols which are essentially odorless and which in addition to the —SH group contain polar groups are also useful in carrying out the present invention, as are compounds capable of hydrolyzing to molecules possessing the thiol group and having the other above-mentioned chracteristics. Within this group the naturally occurring amino acids with thiol substituents are particularly preferred. Exemplary suitable thio compounds are cysteine, homocysteine, penicillamine, thiomalic acid, thiosalicylic acid, 2-mercaptoethylamine hydrochloride, dithiothreitol as well as such N-acyl derivatives as N-acetyl cysteine and N-acetyl homocysteine. Also deemed part of the present invention is the use of thiol derivatives in which the thiol group exists in tautomeric equilibrium with the thione form examples of which are 2-pyridinethiones, and 2-thiobarbiturates, related compounds such as thiourea dioxide; and compounds which can be readily hydrolyzed to one of the useful free thio containing compounds such as homocysteine thiolactone, thiazolidine-2-carboxylic acid, S-cysteine sulfonate sodium, and cysteine-S-phosphate sodium.

It should be noted here that thione compounds as a class do not find universal acceptance for use in the present invention inasmuch as certain members of this class such as thiourea, thiouracil, and methyl thiouracil have been shown to be tumorgenic.

Those thione compounds specifically claimed here are of two types, i.e., 2-pyridine thiones and 2-thiobarbiturates. Under 2-pyridinethiones is meant 2-pyridinethione as well as substituted 2-pyridinethiones, for example, 2-pyridinethione, 1-hydroxy-2-pyridinethione, as well as their respective salts with the preferred salts being those of zinc and tin. The 2-thiobarbiturates include (1) 2-thiobarbituric acid as well as its salts; (2) mono-substituted 2-thiobarbituric acids as well as their respective salts. These mono-substituted 2-thiobarbituric acids may be substituted at either the 1 or 5 positions. Examples of such derivatives are 1-methyl-2-thiobarbituric acid and 5-methyl-2-thiobarbituric acid; (3) Di-substituted 2-thiobarbituric acids as well as their respective salts. Said di-substituted 2-thiobarbituric acids may either be mono substituted at both the 1 and 5 positions or have both substituents at the 5-position. Examples of such di-substituted 2-thiobarbituric acids are: 1-methyl-5-ethyl-2-thiobarbituric acids; 5,5-diethyl-2-thiobarbituric acid (thiobarbital), and sodium 5-ethyl-5-(1 methylbutyl)-2-thiobarbiturate (sodium pentothal).

Phosphorus containing reducing agents useful in the invention include such inorganic salts as hypophosphites including ammonium hypophosphite, alkali, e.g., sodium hypophosphite, and alkaline earth, e.g., calcium hypophosphite; a corresponding phosphite; and organic phosphorus compounds, particularly organic substituted phosphine compounds, meeting the requirements of cosmetic acceptability such as tetrakis (hydroxymethyl) phosphonium chloride.

Stannous and titanous salts which are reducing agents and which meet the aforementioned requirements regarding cosmetic acceptability may also be employed. Such metal salts include stannous chloride, stannous bromide, stannous tartrate, stannous acetate, stannous sulfate, titanous chloride (usually in the form of the hexahydrate), titanous bromide, and the like.

According to a presently preferred embodiment of the invention, the reducing agents are incorporated directly into aluminum salt containing anti-perspirant compositions of otherwise essentially conventional formulation. The reducing agent of the invention is normally employed in an amount of about 0.01 – 10 weight percent, preferably within a range of about 0.5 to 3 weight percent, based on the total weight of the anti-perspirant composition.

The anti-perspirant composition contains an aluminum salt such as aluminum chlorhydrate, aluminum chloride or the like in a range of about 8–30 weight percent although amounts outside this range may also be employed. The compositions may be prepared in known forms such as emulsions, suspensions, creams, lotions and the like. These compositions also contain the usual auxiliary ingredients such as fillers, perfumes, and surfactants. Fabric corrosion inhibitors such as glycine or alanine are preferably also present, for example, in an amount of about 0.1 – 5 weight percent.

The anti-perspirant composition may also be dispensed as an aerosol by mixing a liquid anti-perspirant composition with known propellants such as halogenated hydrocarbons, for example, "Ferons" and "Genetrons", or mixtures of low molecular weight aliphatic hydrocarbons such as a mixture of propane and isobutane. Other known inert propellants such as nitrogen may also be employed.

It has been observed that there is a deodorant effect attributable to the use of the stain preventing reducing agents. It is theorized that the reducing agent ties up available oxygen thereby reducing the amount of oxygen in the axillary regions, which oxygen would otherwise be available to oxidize lipids to odoriferous materials.

The following examples further illustrate the incorporation of the cosmetically acceptable reducing agents of the present invention into anti-perspirant compositions.

EXAMPLE 1

A liquid anti-perspirant with anti-staining properties may be prepared by adding to an aqueous medium 8 to 30% by weight of aluminum chlorhydrate, 1% by weight zinc formaldehyde sulfoxylate, 0.1 to 2% by weight of glycine, 0.1 to 5% by weight of a water soluble non-ionic surface active agent, and 0.1 to 2% by weight of hydroxypropyl methyl cellulose in an aqueous alcoholic medium containing 5 to 30% by weight of ethanol, the cellulose having a methoxy content of 24.6 – 25.4%, a hydroxypropoxy content of 4.8 to 5.4% and a viscosity of about 1200 to about 1800 centipoises in 2% solution in water at 20°C.

EXAMPLE 2

A cream type of anti-perspirant composition was prepared by adding to an aqueous medium 18 percent by weight of aluminum chlorhydrate, 11 percent by weight of glyceryl monostearate, 1 percent by weight of N-(lauroyl-colamino formyl methyl) pyridinium chloride, 2.5 percent by weight of glycine, and 1 percent by weight of sodium sulfite.

EXAMPLE 3

An anti-perspirant lotion is prepared by adding to an aqueous medium 8–30% by weight of aluminum chlorohydrate or other aluminum astringent compound, 1% by weight of ammonium hypophosphite, 0.1 to 2% by weight of glycine, 0.1 to 5% by weight of water soluble non-ionic surface active agent, and 0.1 to 2% by weight of hydroxypropyl methyl cellulose in an aqueous alcoholic medium containing 5 to 30% by weight of ethanol, the cellulose having a methoxy content of 24.6 – 25.4%, a hydroxypropoxy content of 4.5 – 5.4% and a viscosity of about 1200 to about 1800 centipoises in 2% solution of water at 20°C.

EXAMPLE 4

A liquid anti-perspirant composition in the form of a lotion is prepared from 8 to 30% by weight of aluminum chlorhydrate, 1% by weight ammonium bisulfite, 0.1 to 5% by weight of glycine, from about 0.1 to 2% by weight of hydroxypropyl methyl cellulose, and an aqueous solvent medium.

While presently preferred embodiments of the invention have been described with particularity, it would be appreciated that various changes and modifications may readily suggest themselves upon being apprised of the present invention. It is intended to encompass all such changes and modifications as fall within the scope and spirit of the appended claims.

I claim:

1. In an anti-perspirant composition containing as the active ingredient an astringent aluminum salt and a dermatologically-acceptable vehicle, the improvement wherein the composition comprises a cosmetically-acceptable reducing agent in an amount of about 0.01 to 10 percent by weight, based on the total weight of the composition, and sufficient to inhibit staining of fabric in contact with the composition and with perspiration, the reducing agent being water dispersible, essentially odorless, non-irritating to skin and a member selected from the group consisting of:

a. ammonium sulfite, alkali-metal sulfite, alkaline-earth-metal sulfite, zinc sulfite or a mixture thereof;
b. ammonium bisulfite, alkali-metal bisulfite, alkaline-earth-metal bisulfite or a mixture thereof;
c. sodium dithionate, zinc dithionate or a mixture;
d. alkali-metal meta-bisulfite;
e. alkali-metal thiosulfate, alkaline-earth-metal thiosulfate or a mixture thereof;
f. 2-thiobarbituric acid mono-substituted-2-thiobarbituric acid in which a substituent is in the 2- or the 5-position, disubstituted-2-thiobarbituric acid in which each substituent is in one of the 2- and 5-positions or a mixture thereof;
g. 2-pyridinethione;
h. alkylamine bisulfite;
i. sodium formaldehyde bisulfite;
j. sodium formaldehyde sulfoxylate, zinc formaldehyde sulfoxylate or a mixture thereof;
k. acetone sodium bisulfite;
l. cysteine, homocysteine, N-acetyl cysteine, N-acetyl homocysteine, homocysteine thiolactone, S-cysteine sulfonate sodium, cysteine-S-phosphate sodium or a mixture thereof;
m. penicillamine;
n. thiomalic acid;
o. thiosalicylic acid;
p. 2-mercaptoethylamine hydrochloride;
q. dithiothreitol;
r. thiourea dioxide;
s. thiazolidine-2-carboxylic acid;
t. ammonium hypophosphite, alkali-metal hypophosphite, alkaline-earth-metal hypophosphite or a mixture thereof;
u. ammonium phosphite, alkali-metal phosphite, alkaline-earth-metal phosphite or a mixture thereof;
v. tetrakis(hydroxymethyl)phosphonium chloride; and
w. dermatologically-acceptable stannous salt.

2. A composition according to claim 1, wherein said reducing agent is a sulfite selected from the group consisting of ammonium sulfite, alkali sulfite, alkaline earth sulfite and zinc sulfite.

3. A composition according to claim 1, wherein said reducing agent is a bisulfite selected from the group consisting of ammonium, alkali, and alkaline earth bisulfites.

4. A composition according to claim 1, wherein said reducing agent is selected from the group consisting of ammonium hypophosphite, alkali hypophosphite, and alkaline earth hypophosphite.

5. A composition according to claim 1, wherein said reducing agent is a dermatologically acceptable stannous salt.

* * * * *